(12) United States Patent
Fitzmaurice et al.

(10) Patent No.: US 7,576,201 B2
(45) Date of Patent: Aug. 18, 2009

(54) ELECTROCHROMIC COMPOUND

(75) Inventors: Donald Fitzmaurice, Ballsbridge (IE); David Cummins, Navan (IE); David Corr, Lucan (IE); S. Nagaraja Rao, Whitechurch Road (IE); Gerrit Boschloo, Gorssel (NL)

(73) Assignee: Ntera Limited, Dublin (IE)

( * ) Notice: Subject to any disclaimer, the term of this patent is extended or adjusted under 35 U.S.C. 154(b) by 0 days.

(21) Appl. No.: 12/072,876

(22) Filed: Feb. 28, 2008

(65) Prior Publication Data

US 2008/0167465 A1    Jul. 10, 2008

Related U.S. Application Data

(62) Division of application No. 11/049,520, filed on Feb. 1, 2005, now Pat. No. 7,358,358, which is a division of application No. 10/110,245, filed as application No. PCT/IE00/00123 on Oct. 11, 2000, now Pat. No. 6,870,657.

(30) Foreign Application Priority Data

Oct. 11, 1999   (IE) ..................... S990846

(51) Int. Cl.
C07D 241/46        (2006.01)
(52) U.S. Cl. ..................... 544/229; 544/233
(58) Field of Classification Search .......... 544/229, 544/233
See application file for complete search history.

(56) References Cited

U.S. PATENT DOCUMENTS

| | | | |
|---|---|---|---|
| 4,705,854 A | 11/1987 | Leighton | |
| 4,840,893 A | 6/1989 | Hill | |
| 5,329,015 A | 7/1994 | Burk | |
| 5,724,187 A | 3/1998 | Varaprasad | |
| 5,789,592 A | 8/1998 | Gratzel | |
| 6,067,184 A | 5/2000 | Bonhote et al. | |
| 6,301,038 B1 | 10/2001 | Fitzmaurice | |
| 6,605,239 B2 | 8/2003 | Fitzmaurice | |
| 6,755,993 B2 | 6/2004 | Fitzmaurice | |
| 6,861,014 B2 | 3/2005 | Fitzmaurice | |

FOREIGN PATENT DOCUMENTS

| | | |
|---|---|---|
| EP | 0068563 | 1/1983 |
| EP | 0671393 | 9/1995 |
| JP | 0806435 A | 3/1996 |
| SE | 129843 | 10/1950 |
| WO | WO 9735227 | 9/1997 |
| WO | WO 9835267 | 8/1998 |
| WO | 9902621 * | 1/1999 |
| WO | WO 0058781 | 10/2000 |
| WO | WO0063189 | 10/2000 |

OTHER PUBLICATIONS

Anders Hagfeld et al., Nanostructured TiO2 semiconductor electrodes modified with surface: applications for displays and smart windows, SPIE, vol. 2531, pp. 60-69, Jul. 1995.
Richard Dahlbom, "10-Hydroxyalkylphenothiazines," Acta Scandinavica, 6 (1952), 310-311.
Cauquil et al. Compt. Rend. (1947), 225, 578-578.
Cauquil et al. Bulletin de la Societe Chimique de France (1960), 1566-72.

* cited by examiner

*Primary Examiner*—Kahsay T Habte
(74) *Attorney, Agent, or Firm*—Morgan, Lewis & Bockius LLP

(57) ABSTRACT

A compound for electrochromic devices. One such compound of the invention is dihydro-disubstituted phenazine (VI):

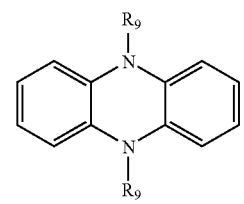

wherein $R_9$ is

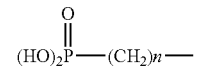

and n=1-10.

1 Claim, No Drawings

ELECTROCHROMIC COMPOUND

CROSS-REFERENCE TO RELATED APPLICATIONS

The present application is a divisional of prior U.S. application Ser. No. 11/049,520, filed 1 Feb. 2005, now U.S. Pat. No. 7,358,358, which is a divisional of U.S. application Ser. No. 10/110,245, filed Sep. 4, 2002, now U.S. Pat. No. 6,870,657, which was the National Stage of International Application No. PCT/IE00/00123, filed 11 Oct. 2000, all of which are hereby incorporated by reference in their entirety.

BACKGROUND

This invention relates to an electrochromic device. In particular, it relates to a nanostructured metal oxide film, doped to metallic levels of conductivity and modified by chemisorption of an electroactive compound, an electrode comprising such a nanostructured film and an electrochromic device comprising such an electrode.

The use of electrochromic devices in applications where optical modulation is required, such as large area static displays and automatically dimmable rear-view mirrors, is well known. Electrochromic devices comprising at least one electrode incorporating a semiconducting nanostructured metal oxide film modified by chemisorption of an electroactive compound are also known, see for example WO-A-97/35227 and WO-A-98/35267.

The device disclosed in WO-A-97/35227 comprises an n- or p-type redox chromophore chemisorbed at the surface of a nanostructured semiconductor electrode, and an auxiliary electroactive compound of the p- or n-type, respectively, which can be oxidised or reduced in a reversible manner, is dissolved in the electrolyte. In the device disclosed in WO-A-98/35267 an n-type redox chrompohore is chemisorbed at the surface of a nanostructured semiconductor electrode and a p-type redox promoter is dissolved in the electrolyte. Although the switching time of these devices is more rapid than that of previously known devices, it is still relatively slow due to the rate-limiting step being the diffusion of the electroactive compound in electrolyte to the relevant electrode. Attempts to eliminate this rate-determining step by adsorbing this compound to the electrode to which it diffuses have only resulted in moderate increases in the rate of switching due to the semiconducting nature of the nanostructured substrate.

While the devices disclosed in WO-A-97/35227 and WO-A-98/35267 are adequate for the applications mentioned above, more rapid switching times would be desirable, especially where dynamic displays, privacy glazing and smart windows are concerned.

BRIEF DESCRIPTION

It is an object of the invention to avoid or minimise the disadvantages of the prior art. It is also an object of the invention to provide an electrochromic device having more rapid switching times than known devices.

According to the invention there is provided a nanoporous, nanocrystalline film comprising a conducting metal oxide having an electroactive compound which is either a p-type or n-type redox promoter or p-type or n-type redox chromophore adsorbed thereto.

A "nanocrystalline film" is constituted from fused nanometer-scale crystallites. To form a conducting film the crystallites are appropriately doped. In a "nanoporous, nanocrystalline" film the morphology of the fused nanocrystallites is such that it is porous on the nanometer-scale. Such films, which may hereinafter be referred to as (conducting/semiconducting) nanostructured films, typically possess a surface roughness of about 1000 assuming a thickness of about 3 μm. Conducting nanostructured films have a resistance of 20 kOhm/square for a 3 μm thick nanostructured Sb doped $SnO_2$ film on a non-conducting substrate at room temperature.

As used herein the term "conducting metal oxide" refers to metal oxides suitably doped to a level that ensures their sheet resistance is less than 100 Kohms per square.

As used herein, the term "electroactive compound" refers to (1) those compounds which are adsorbed at the surface of a conducting nanostructured metal oxide film and are oxidised. If these compounds change colour on being oxidised, they are referred to as p-type redox chromophores. If they do not change colour, they are referred to as p-type redox promoters; and (2) those compounds which are adsorbed at the surface of a semiconducting or conducting nanostructured metal oxide film and are reduced. If these compounds change colour on being reduced, they are referred to as n-type redox chromophores. If they do not change colour, they are referred to as n-type redox promoters.

The invention also provides an electrode for use in an electrochromic device comprising a transparent or translucent substrate bearing an electrically conducting coating which in turn bears a conducting nanostructured metal oxide film according to the invention.

The invention further provides an electrochromic device comprising at least one electrode according to the invention.

DETAILED DESCRIPTION

The electrochromic device of the invention may comprise two electrodes, each comprising a conducting nanostructured metal oxide film according to the invention.

Thus, in one embodiment of the invention, the electrochromic device comprises:

(a) a first electrode comprising a transparent or translucent substrate bearing an electrically conducting coating on its internal face which in turn bears a nanostructured film comprising a conducting metal oxide having an n-type or p-type redox chromophore or n-type or p-type redox promoter adsorbed thereto;

(b) a second or counter electrode comprising a transparent or translucent substrate bearing an electrically conducting coating on its internal face which in turn bears a nanostructured film comprising a conducting metal oxide having a p-type or n-type redox promoter or p-type or n-type redox chromophore adsorbed thereto; and (c) an electrolyte intermediate the electrodes.

In a preferred embodiment, the electrochromic device according to the invention comprises:

(a) a first electrode comprising a transparent or translucent substrate bearing an electrically conducting coating on its internal face which in turn bears a nanostructured film comprising a semiconducting metal oxide having an n-type redox chromophore adsorbed thereto;

(b) a second or counter electrode comprising a transparent or translucent substrate bearing an electrically conducting coating on its internal face which in turn bears a nanostructured film comprising a conducting metal oxide having a p-type redox promoter adsorbed thereto; and (c) an electrolyte intermediate the electrodes.

Alternatively, a p-type redox chromophore may be adsorbed to the conducting metal oxide and an n-type redox promoter is then adsorbed to the semiconducting metal oxide.

In a particularly preferred embodiment of the electrochromic device of the invention, the first electrode is the cathode and the nanostructured film coated thereon comprises $TiO_2$ having an n-type redox chromophore of the formula I, II or III (as defined hereinafter) adsorbed thereto; and the second electrode is the anode and the nanostructured film coated thereon comprises $SnO_2$:Sb having a p-type redox promoter of the formula IV, V, VI or VII (as defined hereinafter) adsorbed thereto.

In another aspect, the invention provides an electrochromic device comprising:

(a) a first electrode comprising a transparent or translucent substrate bearing an electrically conducting coating on its internal face which in turn bears a nanostructured film comprising a conducting or semiconducting metal oxide having an n-type or p-type redox chromophore adsorbed thereto;

(b) a second or counter electrode comprising a transparent or translucent substrate bearing an electrically conducting coating on its internal face which in turn bears a nanostructured film comprising a conducting metal oxide without an electroactive compound adsorbed thereto; and (c) an electrolyte intermediate the electrodes.

In this embodiment, the device will function as an electrochromic device due to the physical properties of the nanostructured film. Firstly, the material has the ability to release electrons and provide these for the reduction of the redox chromophore on the (semi)-conducting metal oxide electrode and secondly, due to the high roughness factor of the film, a large interface between the electrolyte and the film is maintained enabling efficient charge compensation within the device. In a device which has a smooth film, the performance would be less efficient.

In the electrochromic devices of the invention, the following provisos apply:

(1) where the metal oxide is a semiconducting metal oxide, an n-type electroactive compound is adsorbed thereto;

(2) where first and second electrodes both comprise electroactive compounds: (a) the first electrode comprises an n-type redox chromophore and the second electrode comprises a p-type redox promoter or vice versa; or (b) the first electrode comprises an n-type redox promoter and the second electrode comprises a p-type redox chromophore or vice versa; (a) and (b) being subject to proviso (1) above;

(3) where only one of the first and second electrodes comprises an electroactive compound, said compound is an n-type or p-type redox chromophore, subject to proviso (1) above.

The electrodes in the electrochromic device of the invention are preferably spaced apart, for example by a distance of up to 5 mm, preferably at a distance of from 50 μm to 5 mm.

Any suitable n- or p-type redox promoters or redox chromophores may be used in the conducting nanostructured films of the present invention.

Preferred p-type redox promoters and redox chromophores are compounds of the following formulae IV-VII:

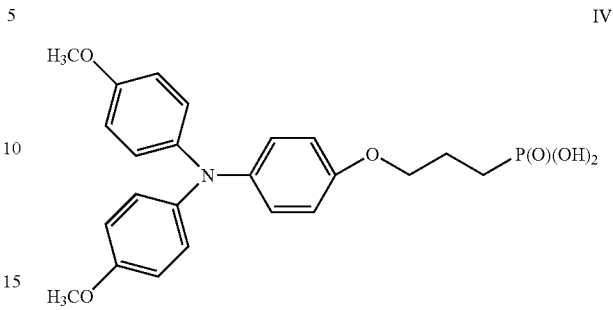

IV

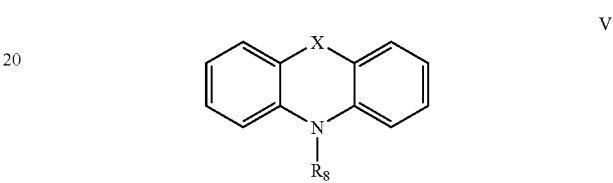

V

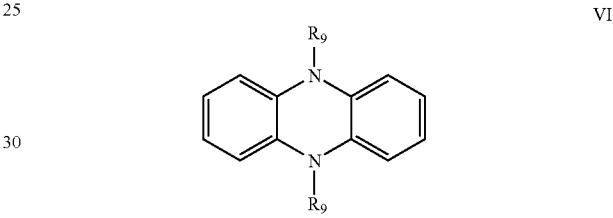

VI

Fe

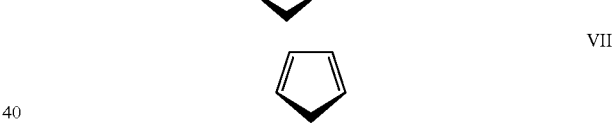

VII wherein X in formula V is S or O and $R_8$-$R_{10}$ are each independently selected from the following:

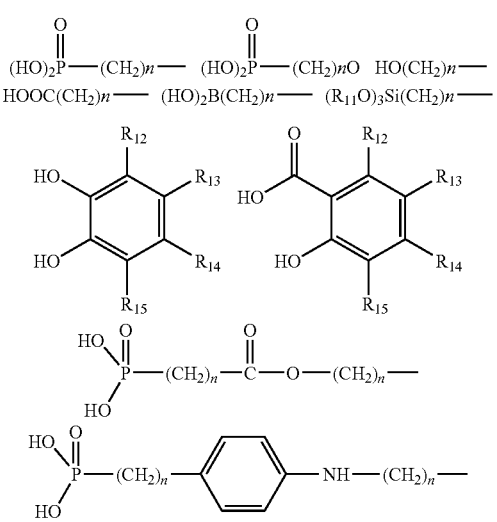

wherein $R_{11}$ is $C_{1-10}$ alkyl and $R_{12}$-$R_{15}$ are each independently hydrogen; $C_{1-10}$ alkyl; $C_{1-10}$ alkylene; optionally substituted aryl; halogen; nitro; or an alcohol group; and n=1-10.

Compounds of the general formulae V, VI and VII are novel and form part of this invention, together with their use in the preparation of conducting nanostructured films, electrodes and electrochromic devices according to the invention.

The compound of the formula IV is known and may be prepared according to conventional procedures as described in *J. Am. Chem. Soc.* 1999, 121, 1324-1336.

Compounds of the general formula V can be prepared by reacting phenothiazine with an alkyl halide terminated with the precursor to or a suitable linker group.

Compounds of the general formula VI can be prepared by reacting an alkyl substituted dihydro-dialkyl phenazine with an alkyl halide terminated with the precursor to or a suitable linker group.

Compounds of the general formula VII can be prepared by reacting a suitably derivatized ferrocene with an alkyl halide terminated with the precursor to or a suitable linker group.

A particularly preferred p-type redox promoter of the general formula V is β-(10-phenothiazyl) propoxy phosphonic acid. This compound (compound VIII) can be prepared according to reaction scheme 1 hereinafter.

The conducting metal oxide used in the nanostructured films of the present invention is preferably selected from any of the following:
(a) $SnO_2$ doped with F, Cl, Sb, P, As or B;
(b) ZnO doped with Al, In, Ga, B, F, Si, Ge, Ti, Zr or Hf;
(c) $In_2O_3$ doped with Sn;
(d) CdO;
(e) Ternary oxides such as $ZnSnO_3$, $Zn_2In_2O_5$, $In_4Sn_3O_{12}$, $GaInO_3$ or $MgIn_2O_4$;
(f) $Fe_2O_3$ doped with Sb;
(g) $TiO_2/WO_3$ or $TiO_2/MoO_3$ systems; and
(h) $Fe_2O_3$/Sb or $SnO_2$/Sb systems.

$SnO_2$ doped with Sb is particularly preferred.

Preferred semiconducting metal oxides which may be used in an electrochromic device of the invention are oxides of titanium, zirconium, hafnium, chromium, molybdenum, tungsten, vanadium, niobium, tantalum, silver, zinc, strontium, iron ($Fe^{2+}$ or $Fe^{3+}$) or nickel or a perovskite thereof. $TiO_2$, $WO_3$, $MoO_3$, ZnO and $SnO_2$ are particularly preferred.

Preferred n-type redox chromophores or redox promoters which may be used in an electrochromic device of the present invention are compounds of the following general formulae I-III:

wherein $R_1$ is selected from any of the following:

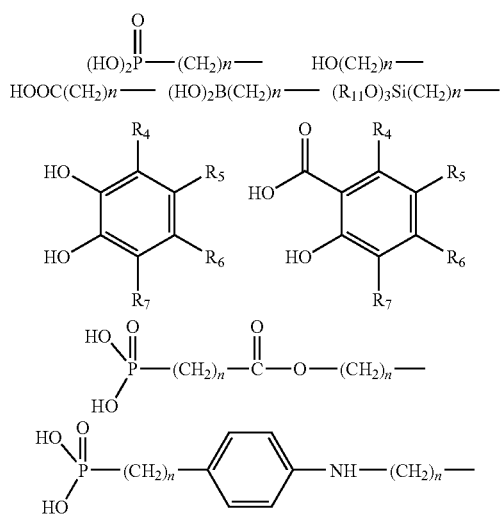

$R_2$ is selected from $C_{1-20}$ alkyl, N-oxide, dimethylamino, acetonitrile, benzyl and phenyl optionally mono- or di-substituted by nitro;

$R_3$ is $C_{1-10}$ alkyl and $R_4$-$R_7$ are each independently selected from hydrogen; $C_{1-10}$ alkyl; $C_{1-10}$ alkylene; aryl or substituted aryl; halogen; nitro; and an alcohol group;

X is a charge balancing ion which is preferably selected from chloride, bromide, iodide, $BF_4^-$, $PF_6^-$ and $ClO_4^-$; and n=1-10.

Compounds of the formulae I, II and III are known and may be prepared in known manner as described in *Solar Energy Materials and Solar Cells*, 57, (1999), 107-125.

A particularly preferred n-type redox chromophore for use in the present invention is a compound of formula I, viz. bis-(2-phosphonoethyl)-4,4'-bipyridinium dichloride.

The conducting and semiconducting metal oxide films may be treated by exposure to a water plasma stream prior to adsorption of the electroactive compounds. Such treatment is useful in promoting reaction of the linker groups, especially siloxane groups, of the electroactive compounds with the hydroxyl groups on the surface of the metal oxide films as it increases the concentration of the latter groups. This treatment also increases the stability of the nanostructured films.

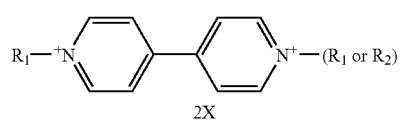

I

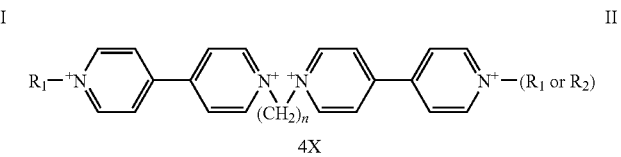

II

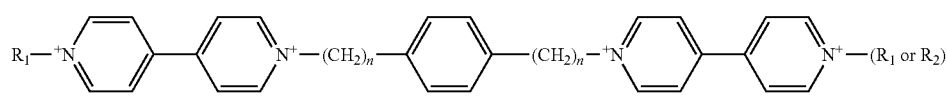

III

The electrode substrates are suitably formed from a glass or plastics material. Glass coated with a conducting layer of fluorine doped tin oxide or indium tin oxide is conveniently used in an electrochromic device of the present invention.

The electrolyte used in the present invention is preferably in liquid form and preferably comprises at least one electrochemically inert salt in solution in a solvent. Examples of suitable salts include lithium salts, such as lithium perchlorate ($LiClO_4$), lithium tetrafluoroborate ($LiBF_4$), lithium iodide (LI), lithium hexafluorophosphate ($LiPF_6$), lithium hexafluoroarsenate ($LiAsF_6$), lithium styrylsulfonate (LiSS), lithium triflate ($LiCF_3SO_3$), lithium methacrylate, lithium halides other than LI, such as lithium chloride (LiCl), lithium bromide (LiBr) and the like, lithium trifluoroacetate ($CF_3COOLi$) and combinations thereof. Of these, $LiClO_4$ or combinations of $LiClO_4$ and $LiBF_4$ are preferred. These sources of alkali metal ions may be present in the electrolyte in a concentration of about 0.1M to 1.0M, with a concentration of about 0.05M to 0.2M being preferred.

Suitable solvents may be selected from acetonitrile, 3-hydroxypropionitrile, methoxypropionitrile, 3-ethoxypropionitrile, 2-acetylbutyrolactone, propylene carbonate, ethylene carbonate, glycerine carbonate, tetramethylene sulfone, cyanoethyl sucrose, γ-butyrolactone, 2-methylglutaronitrile, N,N'-dimethylformamide, 3-methylsulfolane, glutaronitrile, 3,3'-oxydipropionitrile, methylethyl ketone, cyclopentanone, cyclohexanone, benzoyl acetone, 4-hydroxy-4-methyl-2-pentanone, acetophenone, 2-methoxyethyl ether, triethylene glycol dimethyl ether, 4-ethenyl-1,3-dioxalane-2-one, 1,2-butylene carbonate, glycidyl ether carbonates (such as those commercially available from Texaco Chemical Company, Austin, Tex.) and combinations thereof, preferred of which include γ-butyrolactone, propylene carbonate, 1,2-butylene carbonate, the combination of tetramethylene sulfone and propylene carbonate and the combination of 1,2-butylene carbonate and propylene carbonate. γ-Butyrolactone is particularly preferred.

The use of a conducting nanostructured substrate in the electrochromic device of the present invention having a p-type redox promoter or redox chromophore adsorbed thereto, greatly increases the rate of electron transfer from the adsorbed p-type redox promoter or redox chromophore to the positively biased substrate.

Consequently, the switching speed of the electrochromic device is greatly increased. Furthermore, the advantages of an adsorbed p-type redox promoter or redox chromophore, namely low power consumption and extended memory, are maintained.

The invention is illustrated in the following Examples.

EXAMPLE 1

(a) A 2.5 cm×2.5 cm transparent nanostructured semiconductor film, consisting of a 4 μm thick layer of fused $TiO_2$ nanocrystallites, was deposited on a 3.3 cm×3.3 cm fluorine doped tin oxide on glass substrate (15 Ω, 0.5 μm thick, Libby-Owen Ford Tec 15). A colloidal $TiO_2$ dispersion was prepared by hydrolysis of titanium tetraisopropoxide. The average diameter of the initially formed crystallites (7 nm) was increased by autoclaving at 200° C. for 12 hours to 12 nm. Concentrating the autoclaved dispersion to 160 g/l and adding Carbowax (Trade Mark) 20000 (40% wt. equiv. of $TiO_2$) yielded a white viscous sol. (Carbowax 20000 is an ethylene glycol polymer whose average molecular weight is 20000.) A 4 μm thick layer of the above sol was deposited using a screen printing technique on the conducting glass substrate. The resulting gel-film was dried in air for 1 h, sintered in air at 450° C. for 12 h and stored in a darkened vacuum desiccator prior to use. The resulting transparent nanostructured electrodes were 4 μm thick and had a surface roughness of about 1000.

(b) An n-type redox chromophore, bis-(2-phosphonoethyl)-4,4'-bipyridinium dichloride was prepared by adding 4,4'-bipyridine (4.4 g) and diethyl-2-ethylbromo-phosphonate (15.0 g) to water (75 ml). The reaction mixture was refluxed for 72 h and allowed to cool. Following addition of conc. hydrochloric acid (75 ml) the reaction mixture was refluxed for a further 24 h. To recover the product, the reaction mixture was concentrated to 50 ml, isopropyl alcohol (200 ml) added drop-wise, stirred on ice for one hour and filtered. The white crystalline product was washed with cold isopropyl alcohol and air dried to give pure bis-(2-phosphonoethyl)-4,4'-bipyridinium dichloride (12.72 g, 84.24% yield). Calculated for bis-(2-phosphonoethyl)-4,4'-bipyridinium dichloride ($C_{14}H_{20}N_2Cl_2O_6P_2$): C, 37.77; H, 4.53; N, 6.29. Found: C, 35.09; H, 4.49; N, 6.09. $^1$H NMR (water-$d_2$): δ 2.31-2.43 (m, 4H); δ 4.68-4.80 (m, 4H); δ 8.33 (d, unresolved metacoupling, 4H); δ 8.94 (d, unresolved metacoupling, 4H).

(c) $TiO_2$ films, prepared as described above, were modified by chemisorption of a monolayer of the n-type redox chromophore, also prepared as described above, from an aqueous solution (0.02 mol.$dm^{-3}$) over 24 h, washed with distilled isopropanol, dried in air and stored in a darkened vacuum desiccator for 48 h prior to use.

(d) A 2.5 cm×2.5 cm transparent nanostructured $SnO_2$:Sb film was prepared on a 3.3 cm×3.3 cm F-doped tin oxide glass substrate (15 Ω, 0.5 μm thick, supplied by Libby-Owen Ford Tec 15) largely as described in *"Spectroscopy of Highly Doped Nanostructured Tin Dioxide Electrodes"* The Journal of Physical Chemistry, 1999, 103, pp 3093-3098, G. Boschloo and D. Fitzmaurice. Briefly, 10 drops of acetic acid (2.0 mol $dm^{-3}$) were added with stirring to an aqueous dispersion (50 g) of 5 nm diameter Sb-doped $SnO_2$ nanocrystals (15% by wt.$SnO_2$:Sb, supplied by Alfa). The gel which formed immediately was diluted by addition of water (15 ml) and autoclaved at 200° C. for 12 h. Addition of Carbowax 20000 (3.75 g) with stirring for 8 h yielded an amber viscous paste which was diluted with water (10 ml) to make it suitable for spreading. This paste was spread using a glass rod on the conducting glass substrate masked by Scotch tape.

Following drying in air for 1 h the film was fired, also in air, at 450° C. for 12 h. The resulting transparent nanostructured $SnO_2$:Sb films were 3.0 μm thick and had a surface roughness of about 1000.

(e) The p-type redox promoter VIII was prepared as shown in Scheme 1, as follows:

XI: β-(10-phenothiazyl) propionitrile

Triton B (benzyl trimethylammonium hydroxide; 0.6 ml of a 40% aq. soln.) was added dropwise to a solution of phenothiazine (X, 50 g) in acrylonitrile (45 ml) on ice resulting in a vigorous reaction. The reaction mixture was refluxed for 1 h and allowed to cool. The resulting crude product was recrystallized from a 30:70 mixture of hot ethanol and acetone to yield orange crystals of XI, (31.27 g, 49.6%).

XII: β-(10-phenothiazyl) propionic acid

The compound XI (31.27 g) was added to a mixed solvent (350 ml methanol, 105 ml water) NaOH (35 g) solution, refluxed for 15 h and allowed to cool. The crude product was poured on ice water and acidified by the addition of sulphuric acid (2 mol $dm^{-3}$) until a white precipitate formed. The crude product was recrystallised to yield XII, (17.0 g, 52.26%).

XIII: β-(10-phenothiazyl) propionate ester

The compound XII (17 g) was dissolved in 1:2 by vol. mixture of ethanol and toluene (700 ml) acidified by addition of conc. sulphuric acid (4 ml) and refluxed overnight. The solution was concentrated (to approximately 50 ml) and diluted by addition of water (500 ml). The crude product was extracted in ethyl acetate (4×200 ml), washed with water, dried over MgSO$_4$, filtered and the solvent removed under reduced pressure. White crystals of XIII precipitated from the solution on cooling, (11.85 g, 63.9%).

XIV: β-(10-phenothiazyl) propanol

A solution of the compound XIII (11.85 g) in dry diethyl ether (33 ml) was added dropwise to a suspension of LiAlH$_4$ (4.74 g) in dry diethyl ether (70 ml) and stirred overnight at room temperature. Excess LiAlH$_4$ was decomposed by the dropwise addition of water and filtered. Removal of the solvent under reduced pressure gave the green solid XIV, (5.57 g, 54.7%).

XV: β-(10-phenothiazyl) propoxy phosphonic acid dichloride

A solution of XIV (1.0 g) and pyridine (1.0 ml) in dry chloroform (60 ml) was cooled to −15° C. A solution of phosphorous oxychloride (4.73 ml) and pyridine (1.0 ml) and dry chloroform (40 mls) was added dropwise over 0.5 h. The reaction mixture was stirred at −15° C. for 2 h and the resulting homogeneous solution allowed to reach ambient temperature over 1.5 h. The chloroform was removed under reduced pressure and the crude product washed with toluene (3×50 ml) to remove any unreacted phosphorous oxychloride affording a green oil XV, (0.9 g, 65.2%).

VIII: β-(10-phenothiazyl) propoxy phosphonic acid

A solution of XV (0.9 g) in deionised water (60 ml) was stirred overnight. The crude product was extracted in ethyl acetate (4×50 ml), washed with water, dried over sodium sulphate. The white crystals that formed were removed by filtration and the filtrate recrystallized a further 3 times to yield the product VIII, (0.301 g, 40%).

Calculated for VIII (C$_{15}$H$_{16}$O$_4$NSP): C, 53.43; H, 4.76; N, 4.15; P, 9.19. Found: C, 63.58; H, 5.42; N, 4.77; P, 1.86. $^1$H NMR (CDCl$_3$): d 2.24-2.28 (t 2H, J=6.3 Hz); d 3.67-3.70 (t, 2H, J=6.2 Hz); d 4.09-4.12 (t, 2H, J=6.5 Hz); d 6.91-7.19 (m, 8H). $^{31}$P NMR (CDCl$_3$): d 1.69-1.89 (H$_3$PO$_4$); d −11.96

(f) nanostructured SnO$_2$:Sb films, prepared as described above, were modified by chemisorption of a monolayer of the p-type redox promoter VIII, also prepared as described above, from a chloroformic solution (0.02 mol dm$^{-3}$) during 6 h, washed with distilled isopropanol, dried in air and stored in a darkened vacuum desiccator for 24 h prior to use.

(g) A cell, with an internal spacing of about 400 μm, was constructed from a modified TiO$_2$ film and a modified SnO$_2$: Sb film prepared above using a thermoplastic gasket (IP-BOND 2025, supplied by Industria Plastica Monregalese). This gasket had an opening at one corner.

(h) The sandwich structure was evacuated in a modified vacuum desiccator, dipped with the opening in the electrolyte solution, and filled by admitting air into the vacuum desiccator. The electrolyte solution consisted of LiClO$_4$ (0.02 mol dm$^{-3}$) in γ-butyrolactone. It should be noted that both the LiClO$_4$ and γ-butyrolactone were carefully purified and rigorously dried prior to use. Finally, the cell was sealed using a UV-curable epoxy resin.

SCHEME 1

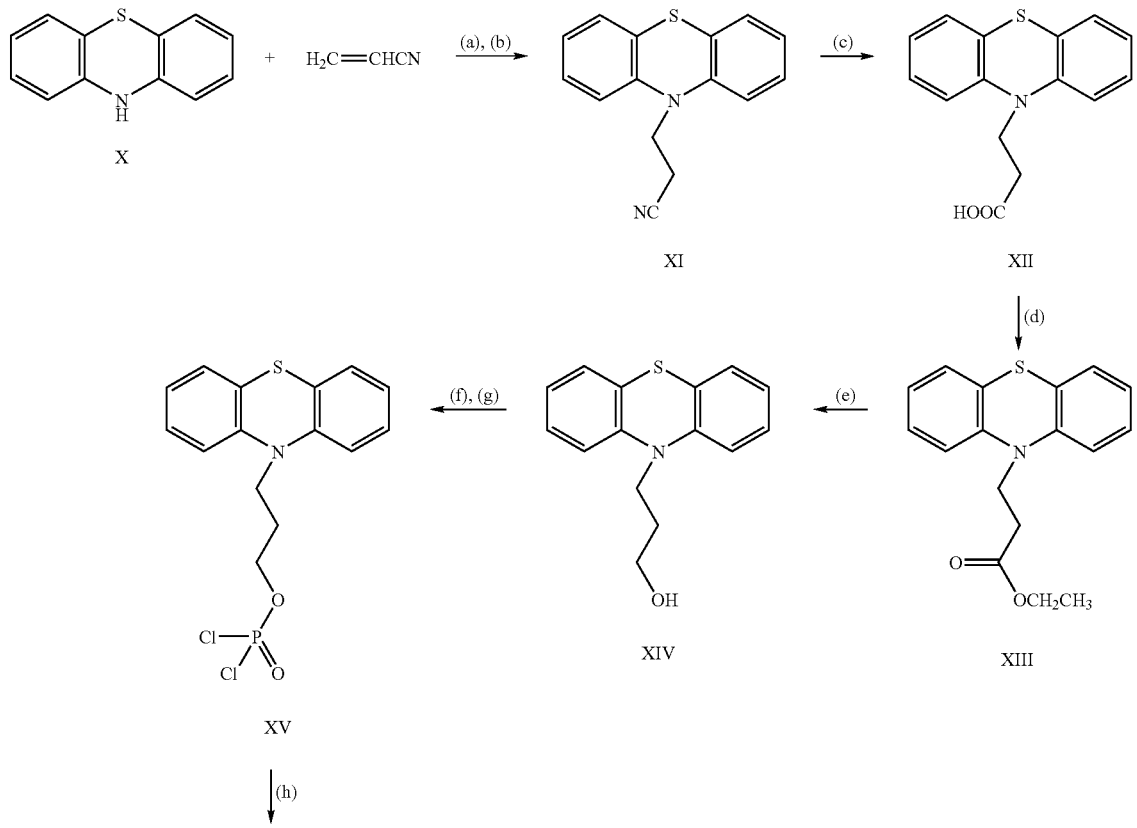

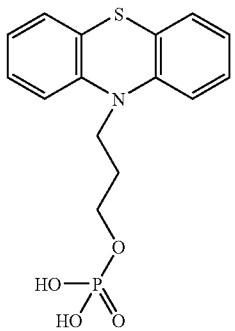

VIII

Reagents and conditions for synthesis for Scheme 1(VIII):
(a) Acrylonitrile, 40%aq. solution benzyl trimethylammonium hydroxide (Triton B),0° c.
(b) reflux 1
(c) Methanolic sodium hydroxide, Reflux 15h.
(d) Ethanol, conc. $H_2SO_4$, Reflux overnight.
(e) $LiALH_4$, Diethyl ether (dry)
(f) Phosphorous oxychloride, stir, -15° c. for 2 h
(g) stir for 1.5 h to bring to ambient temperature
(h) $H_2O$

EXAMPLE 2

(a) Switching Times of Electrochromic (EC) Window

The rate of colouration of the 2.5 cm×2.5 cm EC window assembled as described in Example 1 was measured following application of a voltage of 1.2 V which biased the viologen modified nanostructured $TiO_2$ film negative of the phenothiazine modified $SnO_2$:Sb film. The colouration time, defined as the time taken for the transmittance to decrease by two-thirds of the difference between the steady-state transmittances in the bleached and coloured states, was about 450 ms. The rate of bleaching of the same EC window was measured by reversing the polarity of the voltage applied to the previously coloured device. The bleaching time, defined as the average time taken for the transmittance to increase by two-thirds of the difference between the steady-state transmittances in the coloured and bleached states, was about 250 ms.

The measured colouring and bleaching times are, as far as the inventors are aware, the fastest switching times reported for EC windows of this area.

(b) Colouration Efficiency of EC Window

The peak and steady state currents of the 2.5 cm×2.5 cm EC window were also measured during colouring and bleaching. The peak and steady-state currents measured on colouring were approximately 10 mA $cm^{-2}$ and approximately 30 μA $cm^{-2}$, respectively. The peak and steady-state currents measured on bleaching the same EC window were approximately 16 mA $cm^{-2}$ and approximately 1 μA $cm^{-2}$, respectively. The colouration efficiency $CE(\lambda)$ at 550 nm, defined by Equation (1), was determined from the slope of the plot of the increase in absorbance $\Delta A(\lambda)$ versus the charge accumulated in the device $\Delta Q$. The measured CE (550 nm) was approximately 110 $C^{-1} cm^2$.

$$CE(\lambda) = \frac{\Delta A(\lambda)}{\Delta Q} \quad (1)$$

Both the above peak and steady-state currents are very low and suggest that the power consumption of the EC window will be low and that it should have a long-term memory.

Concerning power consumption, the 2.5 cm×2.5 cm EC window prepared in Example 1 will have an associated steady-state current of approximately 30 μA in the coloured state. This implies that the rate of charge consumption is approximately $2.4×10^{-3}$ $Cs^{-1}$ or approximately $1.5×10^{16}$ electrons $s^{-1}$.

Concerning the long-term memory, if a voltage of 1.2 V is applied to the EC window for 60 s and the circuit opened, the EC window first colours and then bleaches on the time-scale of hours. More quantitatively, the absorbance of the EC window measured at 608 nm takes about 3 h to return to the initially measured value, while the time required for the minimum transmittance in the coloured state to increase by 5% is 600 s.

(c) Stability of EC Window

The stability of the 2.5 cm×2.5 cm EC window prepared in Example 1 was tested under ambient conditions by subjecting it to 10,000 electrochromic cycles. Each electrochromic cycle consisted of applying a potential of 1.2 V, which biases the viologen modified nanostructured $TiO_2$ electrode negative of the phenothiazine nanostructured $SnO_2$:Sb electrode, for 15 s and applying a voltage of 0.00 V for 15 S. The parameters used to characterise cell performance were measured after 1, 10, 100, 1,000 and 10,000 electrochromic cycles and are summarised in Table 1.

TABLE 1

Stability of Window under Electrochromic Cycling

| | Number of Electrochromic Cycles | | | | |
|---|---|---|---|---|---|
| | 1 | 10 | 100 | 1,000 | 10,000 |
| Transmittance in Bleached State (%) | 64 | 61 | 67 | 57 | 64 |
| Transmittance in Coloured State (%) | 13 | 12 | 17 | 14 | 23 |
| Colouring Time (ms) | 460 | 443 | 605 | 448 | 422 |
| Bleaching Time (ms) | 245 | 270 | 215 | 265 | 212 |

TABLE 1-continued

Stability of Window under Electrochromic Cycling

|  | Number of Electrochromic Cycles | | | | |
|---|---|---|---|---|---|
|  | 1 | 10 | 100 | 1,000 | 10,000 |
| Peak Colouring Current (mA cm$^{-2}$) | 10 | 12 | 7 | 12 | 9 |
| Peak Bleaching Current (mA cm$^{-2}$) | 16 | 17 | 17 | 12 | 11 |
| Steady-State Coloured Current (µA cm$^{-2}$) | 33 | 28 | 17 | 13 | 15 |
| Steady-State Bleached Current (µA cm$^{-2}$) | 1 | 2 | 1 | 2 | 1 |
| Colouration Efficiency (C$^{-1}$ cm$^2$) | 110 | 110 | 110 | 110 | 105 |

(a) This test was performed under ambient conditions on a 2.5 cm×2.5 cm device assembled as described in Example 1.

(b) Each electrochromic cycle involved applying a voltage of 1.2 V which biased the viologen modified nanostructured electrode negative of the phenothiazine modified electrode for 15 s and then applying a voltage of 0.0 V for 15 s.

Another aspect of the stability, is the period over which it is possible to maintain the EC window in a coloured state. This aspect of the stability was examined by applying a voltage of 1.2 V, which biases the viologen modified nanostructured TiO$_2$ electrode negative of the phenothiazine nanostructured SnO$_2$:Sb electrode, and which causes the device to colour. This voltage was applied for 15 s and, having determined that the time required for the minimum transmittance to increase by 5% is 180 s, this potential was applied for 15 s every 180 s. This maintained the EC window in the coloured state throughout. It was found that there was no significant degradation after 500 h.

Generally, the findings summarised in Table 1 establish that a 2.5 cm×2.5 cm EC window assembled as described in Example 1 is relatively stable under ambient laboratory conditions over 10,000 electrochromic cycles while the findings summarised above establish that the same window is stable in the coloured state for 500 h.

EXAMPLE 3

Preparation of β-(10-phenothiazyl) propyl-phosphonic acid (illustrated in Scheme 2)

Steps (i)-(v) of Scheme 2 are described in relation to Scheme 1 in Example 1(e).

XVa: β-(10-phenothiazyl) propyl-phosphonate

β-(10-phenothiazyl) propyl chloride IX (5 g, 1.8×10$^{-2}$ M) was refluxed in 5 equivalents of triethyl phosphite for 48 h. The unreacted triethyl phosphite was removed by vacuum distillation to yield the crude product XVa which was taken to the next step without further purification.

$^1$H NMR (chloroform-d): δ 1.17-1.22 (t, 6H, J=7.1 Hz), δ 1.79-1.92 (m, 2H), δ 2.03-2.13 (m, 2H), δ 3.92-4.14 (m, 6H), δ 6.84-7.17 (m, 8H, aromatic)

XVI: β-(10-phenothiazyl) propyl phosphono-trimethyl silyl ester

To an ice cold solution of XVa (0.15 g, 4×10$^{-4}$M) in CHCl$_3$ (dry) was added a cold solution of bromo-trimethylsilane (0.18 g, 1.2×10$^{-3}$ M) in CHCl$_3$ (dry). The reaction mixture was stirred (0° C., 1 h) and then at room temperature for 16 h. The solvent was removed under reduced pressure to yield the crude silyl ester XVI which was taken to the next step without further purification.

$^1$H NMR (chloroform-d): δ 0.00-0.39 (s, 18H), δ 1.75-1.90 (m, 2H), δ 2.00-2.20 (m, 2H), δ 3.84 (m, 2H), δ 6.80-7.20 (m, 8H, aromatic)

XVII: β-(10-phenothiazyl) propyl-phosphonic acid

XVI was stirred in a mixture of 1,4-dioxane: H$_2$O (1:1) at room temperature for 2 h. The resulting precipitate was filtered and dried to yield the crude product XVII $^1$H NMR (methyl sulphoxide-d$_6$): δ 1.55-1.67 (m, 2H), δ 1.78-1.84 (t, 2H), δ 3.91-3.96 (t, 2H, J=7.0 Hz), δ 6.8-7.3 (m, 8H, aromatic)

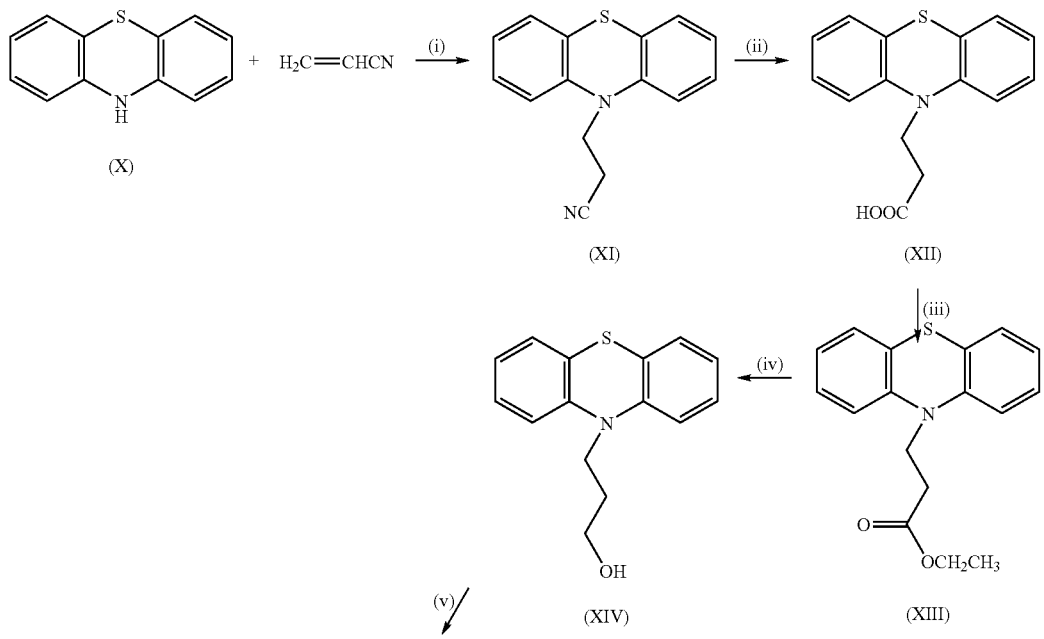

SCHEME 2

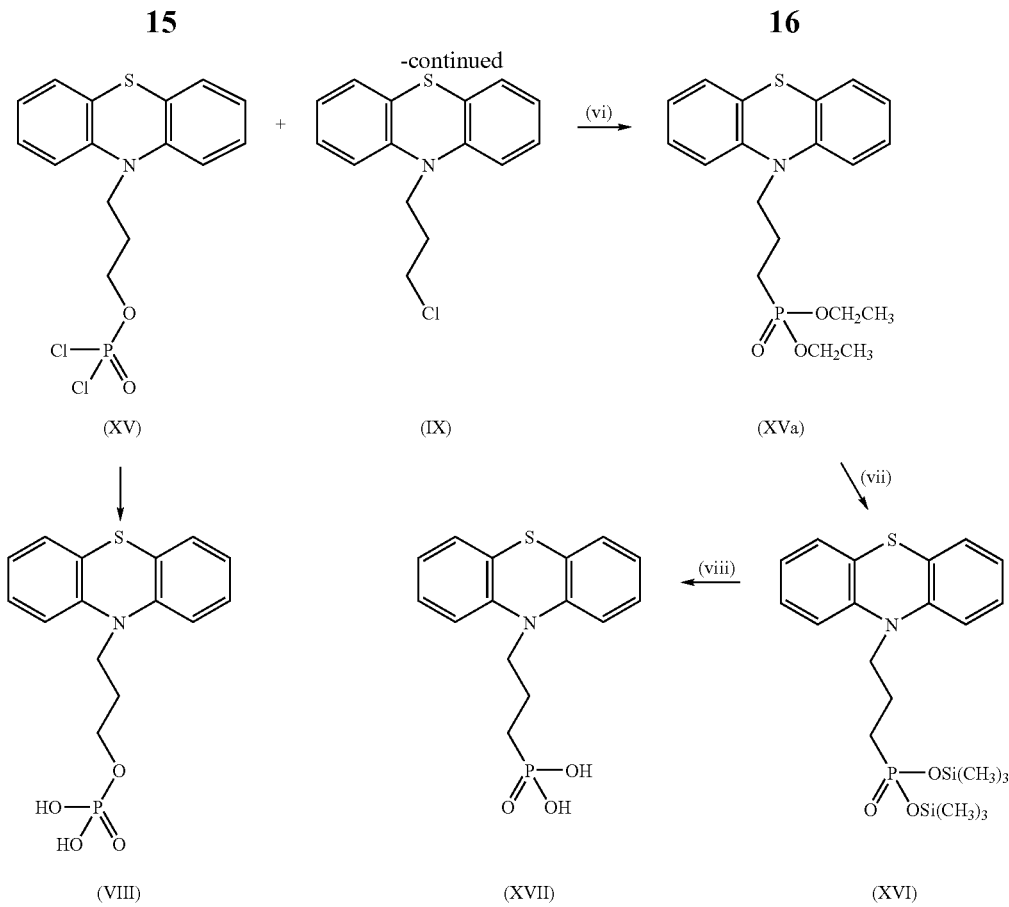

Reagents and conditions for synthesis for Scheme 2 (XVI):
(i) acrylonitrile, Triton B (40% aq. solution), 0° C.; reflux 1 h
(ii) methanolic sodium hydroxide, reflux 15 h;
(iii) ethanol-toluene, conc. $H_2SO_4$, reflux 12 h;
(iv) diethyl ether (dry), $LiAlH_4$;
(v) pyridine-chloroform (dry), phosphorous oxychloride, stir, −15° C., 2 h; stir, RT, 1.5 h;
(vi) triethyl phosphite, reflux, 48 h
(vii) dry chloroform, 0° C.; bromotrimethyl silane, dry chloroform, 0° C.; stir, RT, 16 h
(viii) 1,4-Dioxane/$H_2O$ (1:1), stir, RT, 2 h.

EXAMPLE 4

Preparation of β-(10-phenothiazyl) propionate phosphonic acid (illustrated in Scheme 3)

XXVI: β-(10-phenothiazyl) propionitrile

To an ice cold solution of phenothiazine (XXV, 50 g) in acrylonitrile (45 mL) was added Triton 3 (0.6 mL of a 40% aq. soln.). After some time a vigorous reaction took place. The reaction mixture was heated on a steam bath for 2 h and allowed to cool. The resulting crude solid was crystallized from a 30:70 mixture of hot ethanol and acetone to yield orange crystals of XXVI.

XXVII: β-(10-phenothiazyl) propionic acid

The compound XXVI (20 g) was refluxed for 15 h in 450 mL of methanolic sodium hydroxide(methanol:water, 350: 105 mL). The crude product was poured into ice water and acidified by the addition of sulfuric acid (2 mol $dm^{-3}$). The crude product was crystallized from ethanol to yield XXVII.

$^1$H NMR (chloroform-d): δ 2.66-2.67 (t, 2H, J=7.9 Hz); δ 4.04-4.09 (t, 2H, J=7.9 Hz); δ 6.76-7.05 (m, 8H, aromatic)

XXVIII: β-(10-phenothiazyl) propionic acid chloride

XXVII (1.0 g) was refluxed in 10 mL of oxazyl chloride for 3 h. Removal of oxazyl chloride under low pressure afforded the crude acid chloride XXVIII which was taken for the next step without further purification.

$^1$H NMR (chloroform-d): δ 3.40-3.45 (t, 2H, J=7.9 Hz); δ 4.27-4.32 (t, 2H, J=7.9 Hz); δ 6.87-7.25 (m, 8H, aromatic)

XXIX: β-(10-phenothiazyl) propionate phosphate ester

XXVIII (1.0 g) was dissolved in dry chloroform containing a small quantity of pyridine. Diethyl hydroxy methylphosphonate was added and the reaction mixture was stirred at room temperature overnight. Removal of the solvent under reduced pressure yielded the crude product XXIX which was taken to the next step without further purification.

$^1$H NMR (chloroform-d): δ 1.32-1.37 (t, 2H, J=7.9 Hz); δ 2.93-2.98 (t, 2H, J=7.9 Hz); δ 4.12-4.28 (m, 6H, J=7.9 Hz); δ 4.41-4.44 (d, 2H, J=7.9 Hz); δ 6.89-7.22 (m, 8H, aromatic)

XXX: β-(10-phenothiazyl) propionate phosphono-trimethyl silyl ester

To an ice cold solution of XXIX (1.0 g,) in $CHCl_3$ (dry) was added a cold solution of bromo-trimethylsilane (0.18 g, 1.2× $10^{-3}$ M) in $CHCl_3$ (dry). The reaction mixture was stirred (0° C., 1 h) and then at room temperature for 16 h. The solvent was removed under reduced pressure to yield the crude silyl ester XXX which was taken to the next step without further purification.

¹H NMR (chloroform-d): δ 0.00 (s, 18H); δ 2.93-2.98 (m, 2H); δ 4.23-4.26 (m, 4H, J=7.9 Hz); δ 7.11-7.19 (m, 8H, aromatic)

XXXI: β-(10-phenothiazyl) propionate phosphonic acid

XXX (0.1 g) was stirred in a mixture of 1,4-dioxane: $H_2O$ (1:1) at room temperature for 2 h. The resulting precipitate was filtered and dried to yield the crude product XXXI.

¹H NMR (methyl sulphoxide-$d_6$): δ 2.93-2.98 (m, 2H); δ 4.23-4.26 (m, 4H); δ 7.11-7.19 (m, 8H, aromatic)

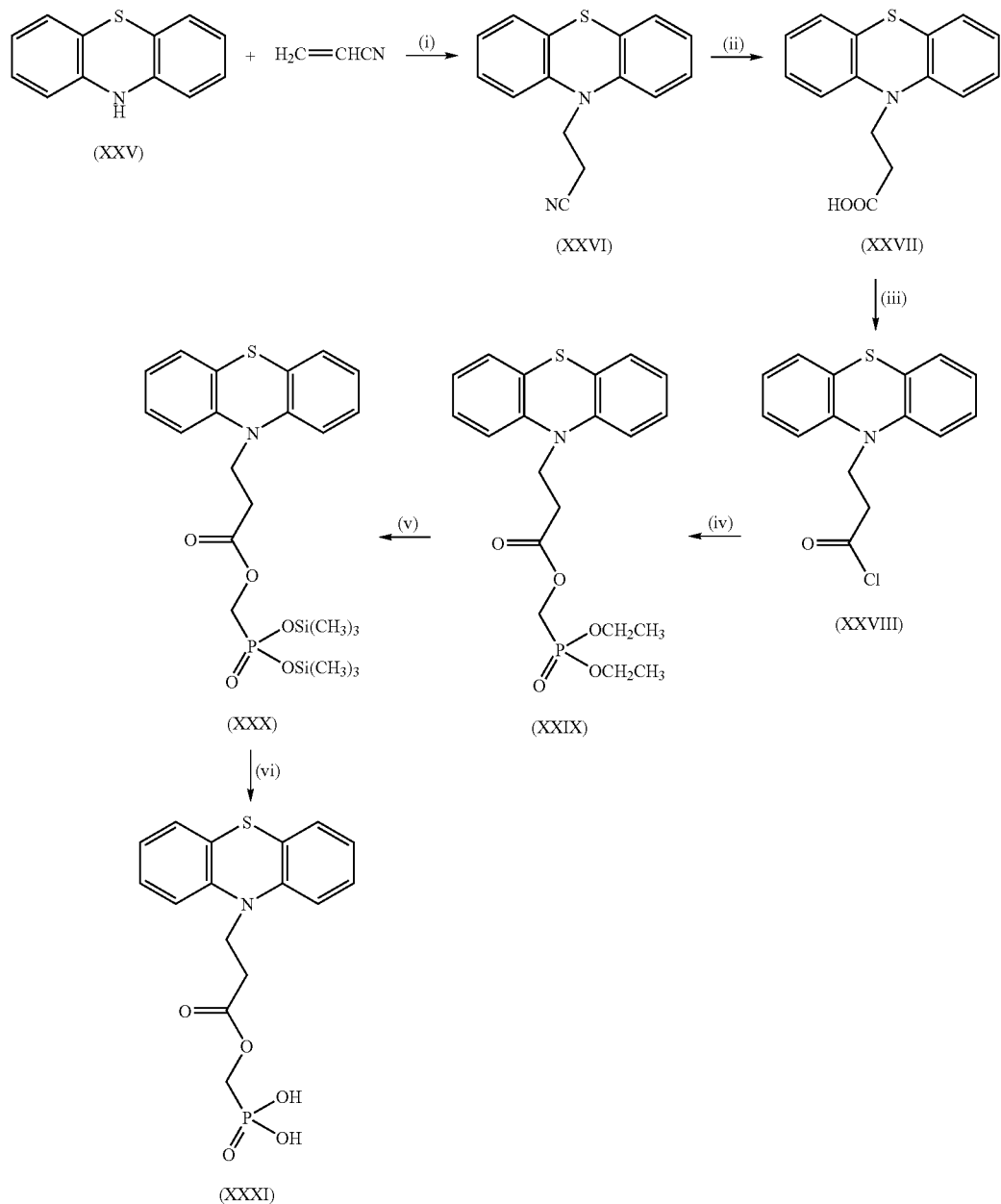

Reagents and Conditions
(i) Triton B, 0° C., 2 h; reflux 2 h
(ii) NaOH, $CH_3OH$, reflux 15 h
(iii) Oxazyl chloride, reflux 3 h
(iv) Diethyl hydroxy methylphosphonate, dry $CHCl_3$/Pyridine, stir r.t.
(v) Bromotrimethylsilane, dry $CHCl_3$, 0° C., stir r.t. 16 h
(vi) 1,4-Dioxane/$H_2O$ (1:1), stir r.t. 2 h

EXAMPLE 5

Preparation of (1-Ferrocenyl) imido-benzylmethyl phosphonic acid (illustrated in Scheme 4)

XXXII: (1-Ferrocenyl) imino-benzyldiethylphosphonate

Ferrocene aldehyde (2.5 g, $1.1 \times 10^{-2}$ M) was dissolved in toluene (80 mL). 4-amino benzyl phosphonate (2.6 g, $1.2 \times 10^{-2}$ M) and a catalytic amount of para-toluene sulphonic acid (0.13 g) was added and the reaction mixture was refluxed for 3 h, in a Dean-Stark setup. The solvent was concentrated under reduced pressure, to yield the crude product XXXII which was taken through to the next step without further purification.

$^1$H NMR (chloroform-d): d 1.25-1.3 (t, 6H, J=7.0 Hz), d 3.13-3.20 (d, 2H, J=21 Hz), d 3.98-4.09 (q, 4H, J=7.0 Hz), d 4.26-4.83 (m, 9H), d 7.12-7.33 (dd, 4H, aromatic), d 8.35 (s, 1H)

XXXIII: (1-Ferrocenyl) imido-benzyldiethylphosphonate

To a warm (50° C.) solution of XXXII (5.39 g, $1.2 \times 10^{-2}$ M) in methanol (80 mL) was added solid NaBH, (0.5 g, $1.2 \times 10^{-2}$ M). A vigorous reaction occurred and the reaction mixture was refluxed for 3 h. The reaction mixture was cooled to room temperature stirred for 16 h. The solvent was removed under reduced pressure, and the crude product was taken up in chloroform (4×50 mL) and dried. The chloroform layer was washed with water and dried. Removal of the solvent afforded the crude product which was purified using column chromatography (100% CHCl$_3$) to yield XXXIII.

$^1$H NMR (chloroform-d): d 1.25-1.30 (t, 6H, J=7.0 Hz), d 3.04-3.11 (d, 2H, J=21 Hz), d 3.99-4.05 (q, 4 H, J=7.0 Hz), d 4.05-4.26 (m, 11H), d 6.62-6.65 (d, 2H, aromatic), d 7.13-7.16 (d, 2H, aromatic)

XXXIV: (1-Ferrocenyl) imdio-benzyldiethyl trimethylsilyl ester

To an ice cold solution of XXXIII (1.0 g, $2 \times 10^{-3}$ M) in CHCl$_3$ (dry, 10 mL) was added a cold solution of bromotrimethylsilane (2.0 g, $1.3 \times 10^{-2}$ M) in CHCl$_3$ (dry, 4 mL). The reaction mixture was stirred (0° C., 1 h) and then at room temperature for 16 h. The solvent was removed under reduced pressure to yield the crude silyl ester XXXIV which was taken to the next step without further purification.

$^1$H NMR (chloroform-d): d 0.00 (s, 18H), d 2.94 (d, 2H, J=21 Hz), d 4.17-4.19 (m, 11H), d 6.79-6.85 (d, 2H, aromatic), d 7.09-7.20 (d, 2H, aromatic)

XXXV: (1-Ferrocenyl) imido-benzylmethyl phosphonic acid

XXXIV was stirred in a mixture of DMF/H$_2$O (1:1) at room temperature for 4 h. The crude product that precipitated was filtered, washed with H$_2$O and dried under vacuum to yield XXXV.

$^1$H NMR (methyl sulphoxide-d$_6$); d 2.71-2.78 (d, 2H, J=21 Hz), d 3.93-4.26 (m, 11H), d 6.53-6.55 (d, 2H, J=7.9 Hz), d 6.92-6.95 (d, 2H, J=7.1 Hz)

$^{31}$P NMR (methyl sulphoxide-d$_6$): d 24.4

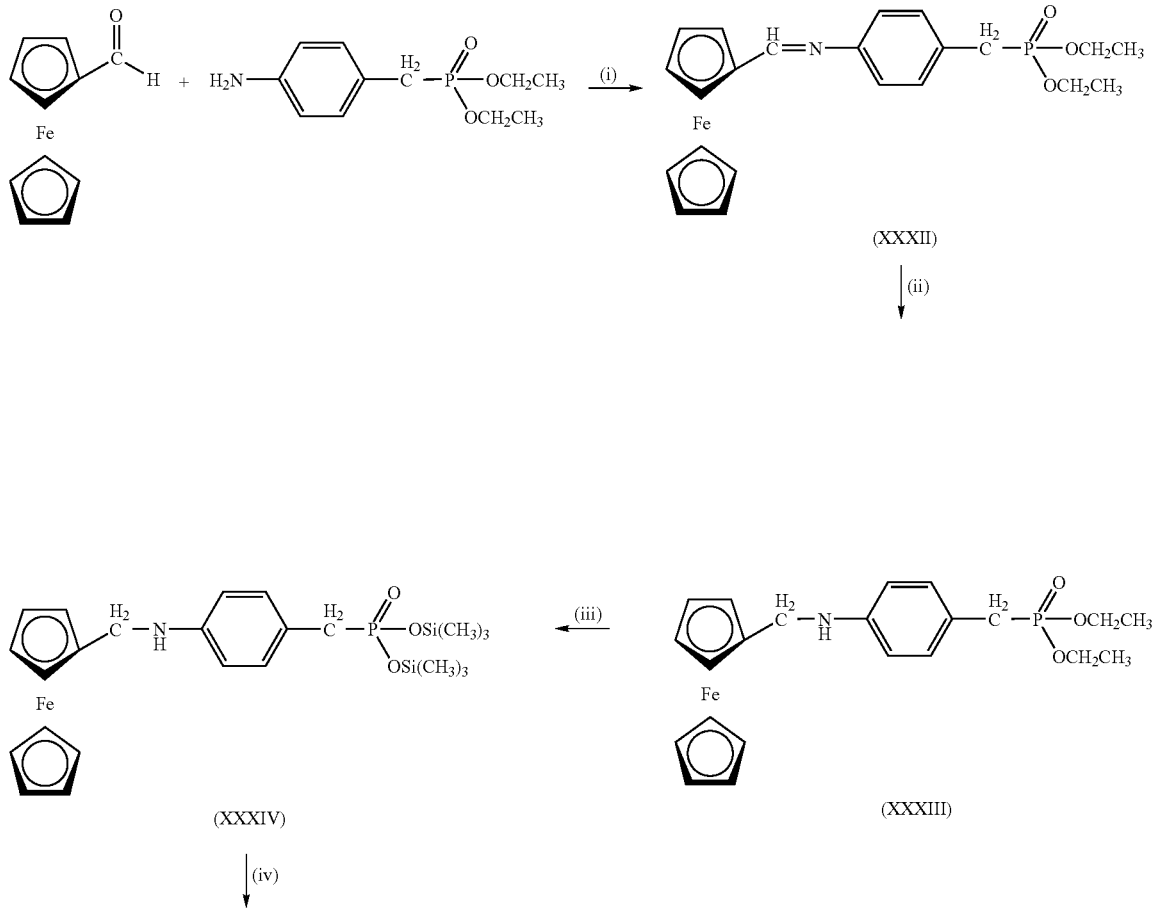

SCHEME 4

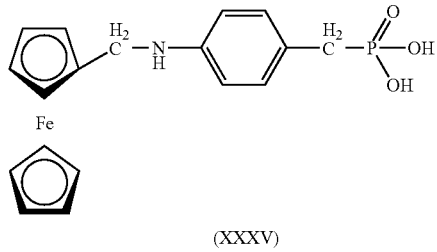

(XXXV)

Reagents and Conditions
(i) Toluene, para-toluene sulphonic acid, reflux 4 h
(ii) Sodium Borohydride, CH₃OH, reflux 3 h
(iii) Bromotrimethylsilane, dry CHCl₃, 0° C., 0.5 h; r.t. 12 h
(iv) Dimethylformamide/H₂O (1:1), r.t. 4 h

EXAMPLE 6

Preparation of β-(10-phenoxazyl) propionate phosphonic acid (illustrated in Scheme 5)

XIX: β-(10-phenoxazyl) propionitrile

To an ice cold solution of phenoxazine (XVII, 50 g) in acrylonitrile (45 mL) was added Triton B (0.6 mL of a 40% aq. soln.). After some time a vigorous reaction took place. The reaction mixture was heated on a steam bath for 2 h and allowed to cool. The resulting crude solid was crystallized from a 30:70 mixture of hot ethanol and acetone to yield orange crystals of XIX.

XX: β-(10-phenoxazyl) propionic acid

The compound XIX was refluxed for 15 h in 450 mL of methanolic sodium hydroxide(methanol:water, 350:105 mL). The crude product was poured into ice water and acidified by the addition of sulfuric acid (2 mol dm$^{-3}$) The crude product was crystallized from ethanol to yield XX.

$^1$H NMR (chloroform-d): δ 2.74-2.80 (t, 2H, J=7.9 Hz); δ 3.90-3.96 (t, 2H, J=7.9 Hz); 6 6.54-6.88 (m, 8H, aromatic)

XXI: β-(10-phenoxazyl) propionic acid chloride

XX (1.0 g) was refluxed in 10 mL of oxazyl chloride for 3 h. Removal of oxazyl chloride under low pressure afforded the crude acid chloride XXI which was taken for the next step without further purification.

$^1$H NMR (chloroform-d): δ 3.19-3.28 (t, 2H, J=7.9 Hz); δ 3.90-3.99 (t, 2H, J=7.9 Hz); δ 6.47-6.90 (m, 8H, aromatic)

XXII: β-(10-phenoxazyl) propionate phosphate ester

XXI (1.0 g) was dissolved in dry chloroform containing a small quantity of pyridine. Diethyl hydroxy methylphosphonate was added and the reaction mixture was stirred at room temperature overnight. Removal of the solvent under reduced pressure yielded the crude product XXII which was taken to the next step without further purification.

$^1$H NMR (chloroform-d): δ 1.35-1.42 (t, 6H, J=6.9 Hz); δ 2.77-2.82 (d, 2H, J=7.3 Hz); δ 3.91-3.96 (d, 2H, J=7.6 Hz); δ 4.11-4.28 (m, 4H); δ 4.41-4.44 (d, 2H, J=8.8 Hz), δ 6.55-6.87 (m, 8H, aromatic)

XXIII: β-(10-phenoxazyl) propionate phosphono-trimethyl silyl ester

To an ice cold solution of XXII (1.0 g,) in CHCl₃ (dry) was added a cold solution of bromo-trimethylsilane (0.18 g, 1.2× 10$^{-3}$ M) in CHCl₃ (dry). The reaction mixture was stirred (0° C., 1 h) and then at room temperature for 16 h. The solvent was removed under reduced pressure to yield the crude silyl ester XXIII which was taken to the next step without further purification.

$^1$H NMR (chloroform-d): δ 0.0 (s, 18H); δ 2.65-2.70 (t, 2H, J=7.6 Hz); δ 3.80-3.86 (m, 2H); δ 4.25-4.36 (t, 2H, J=10.0 Hz); δ 6.44-6.80 (m, 8H, aromatic)

XXIV: β-(10-phenoxazyl) propionate phosphonic acid

XXIII (0.1 g) was stirred in a mixture of 1,4-dioxane: H₂O (1:1) at room temperature for 2 h. The resulting precipitate was filtered and dried to yield the crude product XXIV.

$^1$H NMR (methyl sulphoxide-d₆): δ 2.60-2.67 (m, 4H), δ 3.66-4.20 (t, 2H, J=7.0 Hz), δ 6.49-6.86 (m, 8H, aromatic)

$^{31}$P NMR (methyl sulphoxide-d₆): 24.5

SCHEME 5

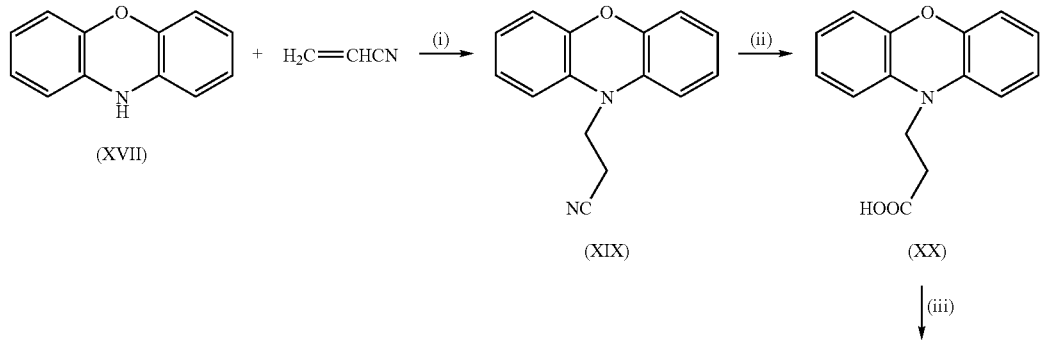

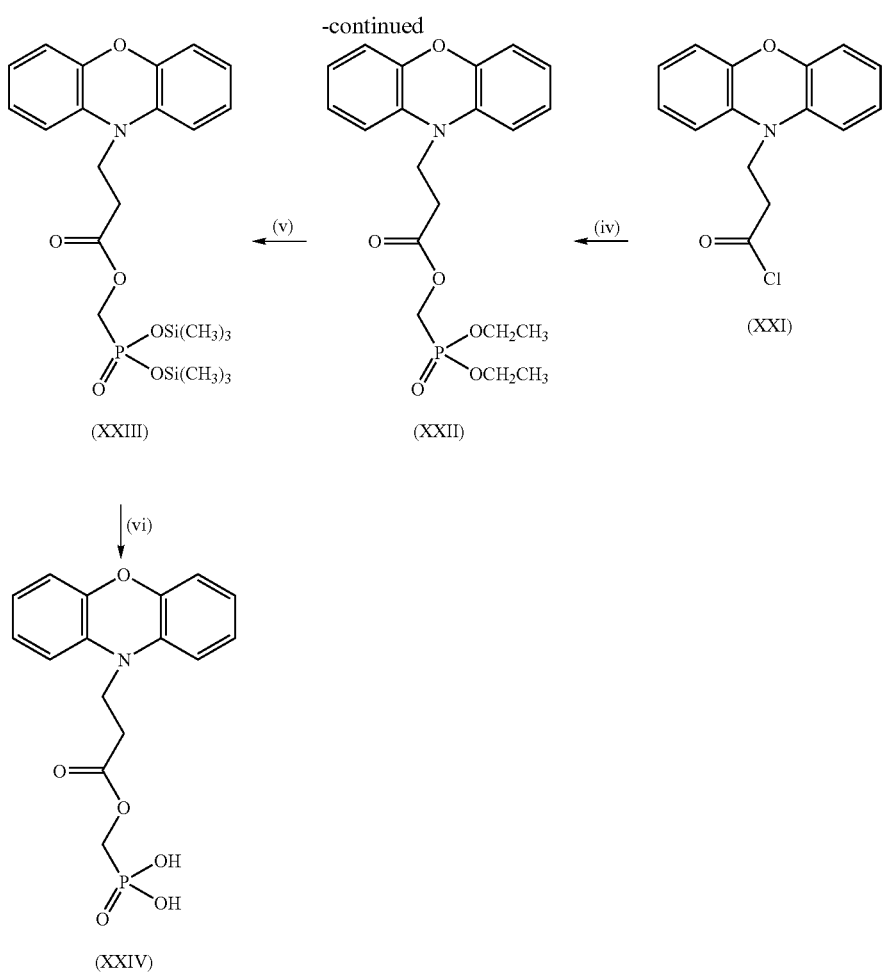

Reagents and Conditions
(i) Triton B, 0° C., 2 h; reflux 2 h
(ii) NaOH, CH₃OH, reflux 15 h
(iii) Oxazyl chloride, reflux 3 h
(iv) Diethyl hydroxy methylphosphonate, dry CHCl₃/Pyridine, stir r.t.
(v) Bromotrimethylsilane, dry CHCl₃, 0° C., stir r.t. 16 h
(vi) 1,4-Dioxane/H₂O (1:1), stir r.t. 2 h

EXAMPLE 7

Stability Tests

Preparation of Nanostructured Electrodes:

All glass was thoroughly cleaned prior to use. Each sheet was manually cleaned using detergent which was thoroughly rinsed off using water. This was then washed with acetone to remove all water present and the acetone was evaporated using hot air. Each film was deposited using a doctor-blading technique. An adhesive stencil was placed over each glass electrode giving the required geometry necessary to leave a perimeter of 5 mm. The glass surface was cleaned with isopropanol and air-dried prior to deposition. A deposit of sol was placed at one end of the glass and manually drawn to the opposite end of the glass with a glass rod (7 mm diameter) leaving an even deposit of the sol. The cathode was a 50 mm×50 mm square TEC 15 glass sheet with nanoporous nanocrystalline titanium dioxide (prepared as in Example 1 (a) except that the films were dried with hot air and sintered in air for 1 h) coated on an area of 40 mm×40 mm square at the centre of the window, leaving an exposed one half centimetre perimeter for sealing materials. The anode was a 50 mm×50 mm square TEC 15 glass sheet with nanoporous nanocrystalline antimony doped tin oxide (prepared as in Example 1 (d) except that the films were dried with hot air and sintered for 1 h) coated on an area 40mm×40mm square at the centre of the window, leaving an exposed one half centimetre perimeter for sealing materials.

Modification of Nanostructured Electrodes

Prior to being modified with the redox compound, the nanostructured cathodes and anodes were placed in an oven at 350° C. to remove any water vapour or organic material. The electrodes were allowed to cool to approximately 80° C. before being placed into the redox compound solutions. All cathodes consisting of a nanostructured $TiO_2$ working electrode where modified by chemisorption of the viologen bis-(2-phosphonoethyl)-4,4'-bipyridinium dichloride from an aqueous solution ($1 \times 10^{-2}$ mol dm$^{-3}$) containing 0.1 M $LiClO_4$ over a 2 h period. Following the derivatisation process, each film was placed horizontally in a wash bath of ethanol for one minute. The washed, derivatised electrodes were dried using hot air.

All anodes consisting of antimony doped tin oxide electrodes were derivatised with a series of six redox promoters giving six sets of six windows as outlined below:

Set A: No redox promoter chemisorbed onto the antimony doped tin oxide electrodes Set B: A solution of β-(10-phenoxazyl) propionate phosphonic acid as prepared in Example 6 (ca. $1 \times 10^{-3}$ M in acetonitrile and $6 \times 10^{-3}$ M $LiPF_6$) were prepared and six windows were immersed for two hours in this solution.

Set C: A solution of β-(10-phenothiazyl) propoxy phosphonic acid as prepared in Example 1(e) (ca. $1 \times 10^{-3}$ M in acetonitrile and $6 \times 10^{-3}$ M $LiPF_6$) was prepared and six windows were immersed for two hours in this solution.

Set D: A solution of β-(10-phenothiazyl) propyl-phosphonic acid as prepared in Example 3 (ca. $1 \times 10^{-3}$ M in chloroform and $6 \times 10^{-3}$ M $LiPF_6$) was prepared and six windows were immersed for two hours in this solution.

Set E: A solution of β-(10-phenothiazyl) propionate phosphonic acid as prepared in Example 4 (ca. $1 \times 10^{-3}$ M in chloroform/acetonitrile (4:1) and $6 \times 10^{-3}$ M $LiPF_6$) was prepared and six windows were immersed for two hours in this solution.

Set F: A solution of (1-ferrocenyl) imido-benzylmethyl phosphonic acid as prepared in Example 5 (ca. $1 \times 10^{-3}$ M in 1:1 chloroform:dimethyl sulfoxide and $6 \times 10^{-3}$ M $LiPF_6$) was prepared and six windows were immersed for two hours in this solution.

Following the derivatisation process, each film was placed horizontally in a wash bath of the respective solvent it was modified from, for one minute. The washed, derivatised electrodes were dried using hot air. The windows were sealed immediately after dying. The cathode and anode were sandwiched together with the electrodes placed in an offset configuration with 2-3 mm offset on two opposite sides to provide an area for an external ohmic contact.

The switching times and stability of each device (A-F) were tested as described in Example 2. The results are shown in Tables 2-7. Optical absorption spectra were recorded using a Hewlett-Packard 8452A diode array spectrophotometer. A Solartron SI 1287 potentiostat was used to record potential-current characteristics. All reported testing was done at room temperature.

TABLE 2

Set A - No Redox Promoter

| | Number of Electrochromic Cycles | | | | | |
|---|---|---|---|---|---|---|
| | 1 | 10 | 100 | 1000 | 3500 | 7000 |
| Transmittance in Bleached State (%) | 69 | 66 | 67 | 68 | 70 | 70 |
| Transmittance in Coloured State (%) | 33 | 31 | 34 | 38 | 46 | 41 |
| Steady-State Coloured Current ($\mu A\ cm^{-2}$) | 290 | 330 | 300 | 290 | 270 | 250 |
| Steady-State Coloured Current ($\mu A\ cm^{-2}$) | 15 | 22 | 21 | 20 | 13 | 23 |
| Colouring Time (ms) | 500 | 500 | 400 | 300 | 300 | 400 |
| Bleaching Time (ms) | 800 | 800 | 500 | 600 | 300 | 400 |

TABLE 3

Set No. B - Phenoxazine

| | Number of Electrochromic Cycles | | | | | |
|---|---|---|---|---|---|---|
| | 1 | 10 | 100 | 1000 | 3500 | 7000 |
| Transmittance in Bleached State (%) | 67 | 67 | 67 | 69 | 69 | 69 |
| Transmittance in Coloured State (%) | 24 | 25 | 23 | 30 | 32 | 36 |
| Steady-State Coloured Current ($\mu A\ cm^{-2}$) | 550 | 2600 | 440 | 380 | 270 | 180 |
| Steady-State Coloured Current ($\mu A\ cm^{-2}$) | 12 | 10 | 16 | 12 | 4 | 10 |
| Colouring Time (ms) | 800 | 800 | 800 | 800 | 800 | 900 |
| Bleaching Time (ms) | 600 | 500 | 600 | 500 | 400 | 400 |

TABLE 4

Set No. C - Phenothiazine (PPPA)

| | Number of Electrochromic Cycles | | | | | |
|---|---|---|---|---|---|---|
| | 1 | 10 | 100 | 1000 | 3500 | 7000 |
| Transmittance in Bleached State (%) | 68 | 67 | 67 | 70 | 68 | 68 |
| Transmittance in Coloured State (%) | 36 | 35 | 35 | 51 | 44 | 46 |
| Steady-State Coloured Current ($\mu A\ cm^{-2}$) | 63 | 62 | 76 | 49 | 38 | 34 |
| Steady-State Coloured Current ($\mu A\ cm^{-2}$) | 11 | 29 | 29 | 12 | 7 | — |
| Colouring Time (ms) | 400 | 500 | 600 | 500 | 400 | 500 |
| Bleaching Time (ms) | 400 | 500 | 600 | 300 | 300 | 400 |

TABLE 5

Set No. D - Alkyl Phenothiazine (PPP)

| | Number of Electrochromic Cycles | | | | | |
|---|---|---|---|---|---|---|
| | 1 | 10 | 100 | 1000 | 3500 | 7000 |
| Transmittance in Bleached State (%) | 66 | 66 | 67 | 66 | 66 | 66 |
| Transmittance in Coloured State (%) | 18 | 18 | 20 | 21 | 24 | 26 |
| Steady-State Coloured Current ($\mu A\ cm^{-2}$) | 1060 | 990 | 860 | 610 | 390 | 320 |
| Steady-State Coloured Current ($\mu A\ cm^{-2}$) | 10 | — | 11 | 12 | 15 | 9 |
| Colouring Time (ms) | 1200 | 1200 | 1300 | 1300 | 1300 | 1200 |
| Bleaching Time (ms) | 500 | 500 | 400 | 500 | 500 | 400 |

TABLE 6

Set No. E - Phenothiazine Ester (PPPE)

| | Number of Electrochromic Cycles | | | | | |
|---|---|---|---|---|---|---|
| | 1 | 10 | 100 | 1000 | 3500 | 7000 |
| Transmittance in Bleached State (%) | 68 | 68 | 67 | 67 | 67 | 68 |
| Transmittance in Coloured State (%) | 20 | 18 | 17 | 17 | 18 | 18 |
| Steady-State Coloured Current ($\mu A\ cm^{-2}$) | 1780 | 1750 | 1700 | 1600 | 1490 | 1390 |
| Steady-State Coloured Current ($\mu A\ cm^{-2}$) | 5 | 9 | 4 | 11 | 13 | 8 |

TABLE 6-continued

Set No. E - Phenothiazine Ester (PPPE)

| | Number of Electrochromic Cycles | | | | | |
|---|---|---|---|---|---|---|
| | 1 | 10 | 100 | 1000 | 3500 | 7000 |
| Colouring Time (ms) | 1000 | 1400 | 900 | 800 | 1000 | 1000 |
| Bleaching Time (ms) | 500 | 500 | 600 | 500 | 500 | 500 |

TABLE 7

Set No. F - Ferrocene (Fc)

| | Number of Electrochromic Cycles | | | | | |
|---|---|---|---|---|---|---|
| | 1 | 10 | 100 | 1000 | 3500 | 7000 |
| Transmittance in Bleached State (%) | 57 | 58 | 58 | 58 | 60 | 61 |
| Transmittance in Coloured State (%) | 16 | 13 | 13 | 15 | 21 | 21 |
| Steady-State Coloured Current ($\mu A\ cm^{-2}$) | 470 | — | 270 | — | 130 | 100 |
| Steady-State Coloured Current ($\mu A\ cm^{-2}$) | 11 | 10 | 7 | 9 | 6 | 6 |
| Colouring Time (ms) | 1000 | 1400 | 900 | 800 | 1000 | 1000 |
| Bleaching Time (ms) | 500 | 500 | 600 | 500 | 500 | 500 |

The tabulated results can be explained as follows:

Transmittance in the bleached state (%)—the percentage of light passing through the device in the colourless state.

Transmittance in the coloured state (%)—the percentage of light passing through the device in the coloured state.

Steady State Current (SSC)—the value of the current when it has reached an equilibrium.

Generally, the findings summarised for A-F in Tables 2-7 establish that a 40×40 mm EC window assembled as described above is stable under ambient laboratory conditions over 7000 electrochromic cycles. The values of the transmittance in the colourless state are generally consistent throughout each test indicating that a large proportion of the incident light is passing through each device even after 7000 cycles. This indicates substantially no optical degradation of the films. The transmittance values in the coloured state are also generally consistent. The dynamic ranges between the transmittance in the colourless state and the transmittance in the coloured state are large which indicate good performance for an EC device. The SSC values for the coloured state are generally less that 25 micro amps $cm^{-2}$. This indicates a very small leakage current. The SSC for the bleached state in each case is of the order of 1 micro amp cm $^{-2}$. These low power consumption readings illustrate the memory effect of the devices as constructed. Furthermore, each device exhibits rapid switching times for both the coloured and colourless states. Colouring times range from 30 to 75 $ms/cm^2$ and bleaching times from 25 to 50 $ms/cm^2$. These times are significantly faster than those obtained with conventional devices which have switching times of at least 1 $s/cm^2$.

The advantages of the EC devices of the invention over previous EC devices are:
1. They are fast switching.
2. They provide deeper colouration.
3. The range of colours is greater.
4. They have low steady state current.

What is claimed is:

1. A compound of the following formula VI:

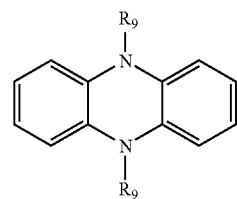

VI wherein $R_9$ is selected from the following:

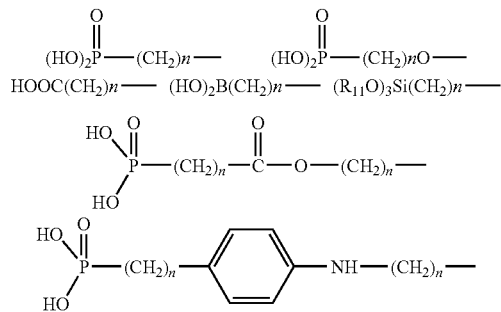

wherein $R_{11}$ is $C_{1-10}$ alkyl; and n=1-10.

* * * * *